US008992960B2

(12) United States Patent
Santra

(10) Patent No.: US 8,992,960 B2
(45) Date of Patent: Mar. 31, 2015

(54) MULTIFUNCTIONAL SILICA-BASED COMPOSITIONS AND GELS, METHODS OF MAKING THEM, AND METHODS OF USING THEM

(75) Inventor: Swadeshmukul Santra, Orlando, FL (US)

(73) Assignee: University of Florida Research Foundation, Inc.

( * ) Notice: Subject to any disclaimer, the term of this patent is extended or adjusted under 35 U.S.C. 154(b) by 893 days.

(21) Appl. No.: 13/074,466

(22) Filed: Mar. 29, 2011

(65) Prior Publication Data

US 2011/0244056 A1   Oct. 6, 2011

Related U.S. Application Data

(60) Provisional application No. 61/319,037, filed on Mar. 30, 2010.

(51) Int. Cl.
| | | |
|---|---|---|
| *A01N 25/28* | (2006.01) | |
| *A01N 31/02* | (2006.01) | |
| *A01N 59/20* | (2006.01) | |
| *B82Y 5/00* | (2011.01) | |
| *A01N 25/34* | (2006.01) | |

(52) U.S. Cl.
CPC . *B82Y 5/00* (2013.01); *A01N 25/28* (2013.01); *A01N 25/34* (2013.01); *A01N 59/20* (2013.01)
USPC ........................... 424/421; 424/630; 514/706

(58) Field of Classification Search
CPC ....... A01N 59/20; A01N 41/12; A01N 25/28; A01N 25/34; A01N 31/02; A61K 33/34; A61K 49/0093; B82Y 5/00
USPC .................................. 424/421, 630; 514/706
IPC ...................................................... A01N 59/20
See application file for complete search history.

(56) References Cited

U.S. PATENT DOCUMENTS

| | | | |
|---|---|---|---|
| 2,913,419 | A | 4/1956 | Alexander |
| 3,983,214 | A | 9/1976 | Misato et al. |
| 3,992,146 | A | 11/1976 | Fazzalari |
| 5,462,738 | A | 10/1995 | LeFiles et al. |
| 5,939,357 | A | 8/1999 | Jones et al. |
| 6,471,976 | B1 | 10/2002 | Taylor et al. |
| 6,548,264 | B1 | 4/2003 | Tan et al. |
| 6,924,116 | B2 | 8/2005 | Tan et al. |
| 7,147,921 | B2 | 12/2006 | Camp et al. |
| 7,163,709 | B2 | 1/2007 | Cook et al. |
| 7,226,610 | B2 | 6/2007 | Winniczuk |
| 7,332,351 | B2 | 2/2008 | Tan et al. |
| 8,221,791 | B1 | 7/2012 | Santra |
| 8,246,933 | B2 | 8/2012 | Jiang et al. |
| 8,361,437 | B2 | 1/2013 | Sharma et al. |
| 2001/0051174 | A1 | 12/2001 | Staats |
| 2004/0067247 | A1 | 4/2004 | De Sloovere et al. |
| 2004/0091417 | A1 | 5/2004 | Yadav |
| 2005/0084438 | A1 | 4/2005 | Do et al. |
| 2006/0018966 | A1* | 1/2006 | Lin et al. ........................ 424/484 |
| 2007/0009672 | A1 | 1/2007 | Jeong et al. |
| 2007/0098806 | A1 | 5/2007 | Ismail et al. |
| 2010/0015236 | A1 | 1/2010 | Magdassi et al. |

OTHER PUBLICATIONS

Dugravot et al. (J Neurophysiol 90:259-270, 2003).*
The International Search Report and Written Opinion dated Jan. 2, 2011.
Kim, Y.H., et al., "Preparation and characterization of the Antibacterial Cu Nanoparticle Formed on the Surface of Si02 Nanoparticles," J. Phys. Chem B 2006, vol. 110, pp. 24923-24928.
Bark, T.K., et al., "Nanosilica-From MEdicine to Pest Control," Parasitol, R es 2008, vol. 103, pp. 253-258.
Tae-Gon Kim, et al. Silver-Nanoparticle Dispersion From the Consolidation of Ag-Attached Silica Colloid, School of Materials Science and Engineering, Seoul National University, Seoul 151-744, Korea, Oct. 4, 2003, 8 pages.
Yeshchenko, Oleg, Influence of Annealing Conditions on Structure and Optical Properties of Copper Nanoparticles Embedded in Silica Matrix, 2006, Physics Department, National Taras Shevchenko Kyiv University, Ukraine, pp. 1-25.
Kikteva, T.A., Probing the Sol-Gel Conversion in the Tetraethoxysilane/Alcohol/Water System with the Aid of Diffusion-Controlled Flourescence Quenching, 1997, Journal of Colloid and Interface Science, vol. 193, pp. 163-166.
Cho. et al.. "The Study of Antimicrobial Activity and Preservative Effects of Nanosilver Ingredient". Electrochimica Acta 51,956-960 (2005).
Feng, et al. "A Mechanistic Study of the Antibacterial Effect of Silver Ions on *Escherichia coli* and *Staphylococcus aureus*", Journal of Biomedical Materials Research 52, 662-668 (2000).
Jasiorski, et al., "Textile with silver Silica Spheres: its Antimicrobial Activity against *Escherichia coli* and *Staphylococcus aureus*", Journal of Sol-Gel Science and Technology 51, 330-334 (2009).

(Continued)

*Primary Examiner* — Abigail Fisher
*Assistant Examiner* — Jessica Kassa
(74) *Attorney, Agent, or Firm* — Thomas Horstemeyer, LLP

(57) ABSTRACT

Briefly described, embodiments of this disclosure, among others, include compositions, gels, methods for synthesizing multifunctional silica based nanoparticle gel, method of treating, preventing, or both treating and preventing, a disease in a plant species, method for simultaneously treating citrus plants for citrus canker and preventing the invasion of an Asian Citrus Psyllid (ACP) vector that carries the pathogen and spreads the citrus greening disease in citrus plants, and the like.

13 Claims, 3 Drawing Sheets

(56) References Cited

OTHER PUBLICATIONS

Lu, et al., "A Simple and Effective Route for the Synthesis of Crystalline Silver Nanrods and Nanowires", Advanced Functional Materials 14, 183-189 (2004).

Solomon, et al. (2007). "Synthesis and study of silver nanoparticles." Journal of Chemical Education. 84, 322-325.

Pal, et al. (2007). "Does the antibacterial activity of silver nanoparticles depend on the shape of the nanoparticle? A study of the gram-negative bacterium *Escherichia coli*." Applied Environmental Microbiology 73, 1712-1720.

Jung, et al. (2008). Antibacterial activity and mechanism of action of the silver ion in *Staphylococcus aureus* and *Escherichia coli*. Applied Environmental Microbiology 74, 2171-2178.

Frisken, B. J. (2001 ). "Revisiting the method of cumulants for the analysis of dynamic light-scattering data." Applied Optics 40, 4087-4091.

Schillinger, et al. (1989). "Antibacterial Activity of *Lactobacillus-sake* Isolated from Meal." Applied and Environmental Microbiology 55, 1901-1906.

Rastogi, et al., "Ag colloids and Ag clusters over EDAPTMS-coated silica nanoparticles:synthesis, characterization, and antibacterial activity against *Escherichia coli*." Nanomedicine-Nanotechnology Biology and Medicine 7, 305-314 (2011 ).

Collins, T.J., "ImageJ for Microscopy Biotechniques." 43, 25-30(2007).

Naik, et al., "Biomimetic synthesis and patterning of silver nanoparticles." Nature Materials 1, 169-172 (2002).

Mock, et al., "Shape effects in plasmon resonance of individual colloidal silver nanoparticles." Journal of Chemical Physics 116, 6755-6759 (2002).

Manipradad, et al.; Novel Copper (Cu) Loaded Core-Shell Silica Nanoparticles with Improved Cu Bioavailability: Synthesis, Characterization and Study of Antibacterial Properties; Journal of Biomedical Nanotechnology; vol. 8, 1-9, 2012.

Maniprasad, et al.; Antimicrobial Properties of Copper and Silver Loaded Silica Nanomaterials; Manuscript ID No. 1198620; to be submitted to the 36th International Conference on Advanced Ceramics and Composites (ICACC); Apr. 4, 2012.

H.W. Richardson, "Handbook of Copper Compounds and Applications" Copper Fungicides/batericides H.W. Richardson Editor, 1997, Marcel Dekker, Inc.: New York, NY, pp. 93-122.

Torgeson D.C .. ed. "Fungicides-An Advanced Treatise" Agricultural and Industrial Applications and Enviromental Interaction. vol. 1. 1967. Academic Press: New York. NY, Ch. 6, p. 153-193 [chapter Title: Formulation: Author: E. Somers.

Navarro, E., et al., in "Environmental behavior and ecotoxicity of engineered nanoparticles to algae, plants, and fungi," Ecotoxicology, 2008, 17(5): pp. 372-386.

Oberdorster, G., et al., in Nanotoxicology: An Emerging Discipline Evolving from Studies of Ultrafine Particles, Environmental Health Perspectives, 2005, 113(7): pp. 823-839.

S. Santra, et al., in "Fluorescence Lifetime Measurements to Determine the Core-Shell Nanostructure of FITC-doped Silica Nanoparticles: An Optical Approach to Evaluate Nanoparticle Photostability" Journal of Luminescence, 2006, 117(1) pp. 75-82.

Zhang, K., Synthesis and Characterization of Silica-Copper Oxide Composite Derived from Microemulsion Processing, 1999, Langmuir, vol. 15, pp. 3056-3061.

Zhang, X. A New Solution Route to Hydrogen-terminated Silicon Nanoparticles: Synthesis, Functionalization and Water Stability, Jan. 2007, Nanotechnology, vol. 18, pp. 1-6.

* cited by examiner

MULTIFUNCTIONAL SILICA-BASED COMPOSITIONS AND GELS, METHODS OF MAKING THEM, AND METHODS OF USING THEM

CROSS-REFERENCE TO RELATED APPLICATIONS

This application claims priority to U.S. Provisional Patent Application Ser. No. 61/319,037, entitled "MULTIFUNCTIONAL SILICA-BASED NANO-FORMULATIONS" filed on Mar. 30, 2010, which is hereby incorporated by reference.

STATEMENT REGARDING FEDERALLY SPONSORED RESEARCH OR DEVELOPMENT

This invention was made with Government support under Agency contract no. EEC-0506560 awarded by the National Science Foundation. The Government has certain rights in this invention.

BACKGROUND

The worldwide citrus industry is currently battling with two potentially devastating diseases: citrus greening, also known as Huanglongbing or HLB, and citrus canker.

Citrus greening is the most destructive, highly infectious disease of most commercial citrus varieties. This disease is caused by the Gram-negative HLB bacterium that belongs to the genus *Candidatus Liberibacter* as reported by J. M. Bove in "Huanglongbing: A destructive, newly-emerging, century-old disease of citrus," *Journal of Plant Pathology* 2006, 88, (1), 7-37. HLB threatens the citrus industry worldwide and may cause damage to the citrus industry and economy in the State of Florida. The problem can be severe and kill citrus trees. The disease causes fruits to taste bitter and become deformed, small-sized and poorly-colored, making it unusable and unmarketable. Currently, there is no cure for the HLB.

The Asian Citrus Psyllid (ACP) is an invasive phloem-feeding insect that causes serious damage to citrus plants and citrus plant relatives. Burned tips and twisted leaves result from an infestation of ACP on new growth. In addition, ACP is a vector of HLB and carries HLB and can rapidly spread the disease from one grove to another.

Integrated pest management strategies that include the use of disease-free nursery trees, rapid removal of symptomatic trees and aggressive control of ACPs using foliar insecticides have been the primary focus to manage HLB infected groves according to A. Morris et al. in "Economic tradeoffs of citrus greening management" *Citrus Industry* 2008, 89 (4), 26-28 and P. L. Hollis in "Scientists combining efforts to combat greening in Florida's citrus industry" *Southeast Farm Press* 2008, 35 (15), 35.

Unfortunately, the use of foliar insecticides appears to be the only solution available to growers these days to prevent HLB infection, even though such integrated practices are expensive and labor extensive.

Citrus canker is another serious disease, caused by the bacterium *Xanthomonas axonopodis* pv. *citri*, that affects most commercial citrus varieties and has caused economic loss world-wide according to T. R. Gottwald in "The citrus canker epidemic in Florida: The scientific basis of regulatory eradication policy for an invasive species," *Phytopathology* 2001, 91, (1), 30-34. Canker causes necrotic lesions on various parts of trees that include fruits, leaves and stems. The severity of the disease or infection is manifested as defoliation, premature fruit drop, blemished fruit and general tree decline as reported by J. H. Graham in "*Xanthomonas axonopodis* pv. *citri*: factors affecting successful eradication of citrus canker," *Molecular Plant Pathology* 2004, 5, (1), 1-15 and A. K. Das in "Citrus Canker—A review," *J. Appl. Hort.* 2003, 5 (1), 52-60.

While there is no cure for the HLB disease, canker losses have been controlled by the use of appropriate anti-bacterial agents such as copper (Cu) based compounds, including, but not limited to, Cu oxychloride, Cu sulphate, Cu hydroxide, Cu oxide, ammonia-Cu carbonate, antibiotics, such as, streptomycin, tetracycline, and induced systemic resistance compounds, including, acibenzolar-S-methyl, harpin protein. To date, copper (Cu) has been the gold standard for controlling citrus canker disease worldwide due to its effectiveness in protecting against the possibility of infection and minimal development of Cu resistance by a pathogen.

Due to destructive nature of HLB and citrus canker diseases, there is a need to find solutions to combat HLB and citrus canker diseases.

SUMMARY

Briefly described, embodiments of this disclosure, among others, include compositions, gels, methods for synthesizing multifunctional silica based nanoparticle gel, method of treating, preventing, or both treating and preventing, a disease in a plant species, method for simultaneously treating citrus plants for citrus canker and preventing the invasion of an Asian Citrus Psyllid (ACP) vector that carries the pathogen and spreads the citrus greening disease in citrus plants, and the like.

An exemplar embodiment of a composition, among others, includes a multifunctional silica based nanoparticle including a first component and a second component, wherein the first component functions as an antibacterial, an antifungal, or a combination thereof, wherein the second component functions as a repellant for insects.

An exemplar embodiment of a gel, among others, includes, a plurality of multifunctional silica based nanoparticles as described herein are disposed in an amorphous silica material, wherein the amorphous silica material includes one or both of the first component and the second component.

An exemplar embodiment of a method for synthesizing multifunctional silica based nanoparticle gel, among others, includes, adding a portion of loaded silica nanoparticle to an aqueous reaction medium to form mixture I; adding a portion of a second component directly to the aqueous reaction medium containing mixture I to form mixture II; and mixing mixture II to form a multifunctional silica nanoparticle gel that includes multifunctional silica nanoparticles as described herein.

An exemplar embodiment of a method for synthesizing multifunctional silica based nanoparticle gel, among others, includes, adding a portion of powdered loaded silica nanoparticle to a reaction vessel; adding a portion of a second component directly to the powder to form mixture A; and mixing mixture A to form a multifunctional silica nanoparticle gel that includes multifunctional silica nanoparticles as described herein.

An exemplar embodiment of a method of treating, preventing, or both treating and preventing, a disease in a plant species, among others, includes, administering a composition including multifunctional silica based nanoparticles as described herein, multifunctional silica based nanoparticle gel as described herein, or a mixture thereof, to a the plant.

An exemplar embodiment of a method for simultaneously treating citrus plants for citrus canker and preventing the invasion of an Asian Citrus Psyllid (ACP) vector that carries the pathogen and spreads the citrus greening disease in citrus plants, among others, includes, administering a composition including multifunctional silica based nanoparticles as described herein, multifunctional silica based nanoparticle gel as described herein, or a mixture thereof, to a the citrus plant, wherein administering includes covering the leaves and branches of the citrus plant.

Other compositions, gels, methods, features, and advantages of this disclosure will be or become apparent to one with skill in the art upon examination of the following drawings and detailed description. It is intended that all such additional apparatuses, systems, methods, features, and advantages be included within this description, be within the scope of this disclosure, and be protected by the accompanying claims.

DETAILED DESCRIPTION

Figure 1A:
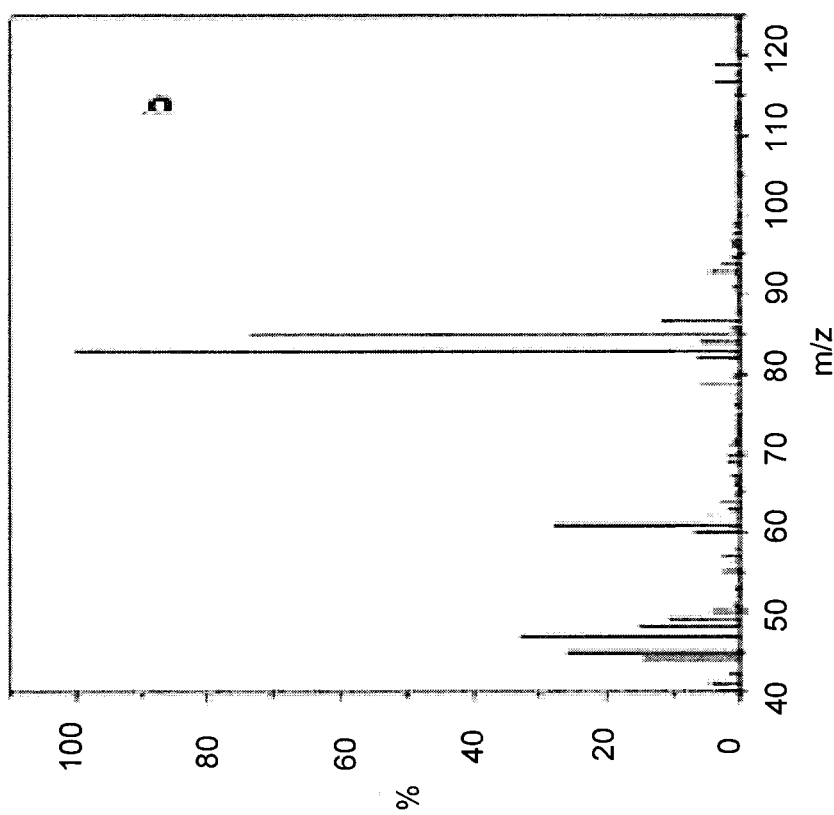
FIG. 1a is a plot of gas chromatography-mass spectroscopy (GC-MS) data of DMDS (control).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, botany, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

DEFINITIONS AND ABBREVIATIONS

Si is used herein to mean silicon dioxide, which is also commonly known as "silica."

NG stands for "Nanogel", which is the gel-like substance formed by the interconnection of nanoparticles, for example, the interconnection of multifunctional silica based nanoparticles.

NP stands for "Nanoparticle", which can have a particle size (e.g., diameter for spherical or substantially spherical nanoparticles) of about 10 to 500 nm, about 10 to 250 nm, about 10 to 100, or about 10 nm to 50 nm. The diameter can be varied from a few nanometers to hundreds of nanometers by appropriately adjusting synthesis parameters, such as amounts of silane precursor, amounts of hydrolyzing agents, polarity of reaction medium, and the like.

CuSiNP stands for copper loaded silica nanoparticle.

CuSiNG stands for copper loaded silica nanogel.

HCuSiNG stands for hybrid Cu-loaded silica nanogel, where the SiNG matrix is loaded with a second silane compound to achieve uniform or substantially uniform plant surface coverage.

Kocide® 3000 pesticide/bactericide; Kocide is a registered trademark of E.I. du Pont de Nemours and Company.

"Uniform plant surface coverage" refers to a uniform and complete (e.g., about 100%) wet surface due to spray application of embodiments of the present disclosure. In other words, spray application causes embodiments of the present disclosure to spread throughout the plant surface.

"Substantial uniform plant surface coverage" refers to about 70%, about 80%, about 90%, or more uniform plant surface coverage.

"Substantially covering" refers to covering about 70%, about 80%, about 90%, or more, of the leaves and branches of a plant.

"Plant" refers to trees, plants, shrubs, flowers, and the like as well as portions of the plant such as twigs, leaves, stems, and the like. In a particular embodiment, the term plant includes a fruit tree such as a citrus tree (e.g., orange tree, lemon tree, lime tree, and the like).

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, n-octyl, dodecyl, octadecyl, amyl, 2-ethylhexyl, and the like. Alkyl can include alkyl, dialkyl, trialkyl, and the like.

As used herein, "treat", "treatment", "treating", and the like refer to acting upon a disease or condition with a multifunctional silica based nanoparticle or gel of the present disclosure to affect the disease or condition by improving or altering it. In addition, "treatment" includes completely or partially preventing (e.g., about 70% or more, about 80% or more, about 90% or more, about 95% or more, or about 99% or more) a plant form acquiring a disease or condition. The phrase "prevent" can be used instead of treatment for this meaning. "Treatment," as used herein, covers one or more treatments of a disease in a plant, and includes: (a) reducing the risk of occurrence of the disease in a plant predisposed to the disease but not yet diagnosed as infected with the disease (b) impeding the development of the disease, and/or (c) relieving the disease, e.g., causing regression of the disease and/or relieving one or more disease symptoms.

The term "antibacterial" refers to a compound or composition that destroys bacteria, suppresses or prevents bacteria growth, and/or suppresses, prevents or eliminates the ability of bacteria to reproduce.

The term "antifungal" refers to a compound or composition that destroys fungus, suppresses or prevents fungus growth, and/or suppresses, prevents or eliminates the ability of the fungus to reproduce.

Discussion:

Embodiments of the present disclosure include multifunctional silica based nanoparticles, methods of making multifunctional silica based nanoparticles, multifunctional silica based nanoparticle gels, methods of making multifunctional silica based nanoparticle gels, methods of using methods of making multifunctional silica based nanoparticle and methods of making multifunctional silica based nanoparticle gels, methods of treating plants, and the like. Embodiments of the present disclosure provide for a composition that can be used for multiple purposes. Embodiments of the present disclosure are advantageous in that they can slowly release one or more agents that can be used to prevent or substantially prevent and/or treat or substantially treat a disease or condition in a plant, act as an antibacterial and/or antifungal, and/or act as a repellent to certain types of insects. Another advantage of an embodiment of the present disclosure is that the agent(s) can be controllably released over a long period of time (e.g., from the day of application until a few weeks or months (e.g., about 6 or 8 months)). Embodiments of the present disclosure and features and advantages of these embodiments will be discussed in further detail herein.

Embodiments of the multifunctional silica based nanoparticle can include a first component and a second component. In addition, embodiments of the present disclosure can include a multifunctional silica based nanoparticle gel that includes multifunctional silica based nanoparticles. The multifunctional silica based nanoparticle and/or multifunctional silica based nanoparticle gel can be included in a composition to be administered (e.g., spraying) to a plant. The multifunctional silica based nanoparticle gel includes multifunctional silica based nanoparticles inter-connected in an amorphous silica material. The nanoparticles can be inter-connected covalently (e.g., through —Si—O—Si— bonds), physically associated via Van der Waal forces, and/or through ionic interactions (e.g., positively charged copper ions and negatively charged silica nanoparticles). The first and second components can be within the amorphous material as well as in the multifunctional silica based nanoparticle.

The first component can function as an antibacterial and/or antifungal, specifically, treating, substantially treating, preventing or substantially preventing, plant diseases such as citrus greening (HLB) and citrus canker diseases. The first component (e.g., Cu) can be released from the multifunctional silica based nanoparticle or gel so that it can act as an antibacterial and/or antifungal for a period of time (e.g., from application to days to months). The second component functions as a repellant for insects that can harm plants and/or carry bacteria, diseases, fungi, and the like, that can harm plants (e.g., fruit tree). The second component (e.g., a sulfur compound) of the multifunctional silica based nanoparticle or gel can act as an Asian Citrus Psyllid (ACP) repellant for a period of time (e.g., from application to days to months). Embodiments of the present disclosure have multifunctional purposes to combat diseases in plants such as trees, bushes, and the like, for example, simultaneously treating, substantially treating, preventing and/or substantially preventing citrus greening and citrus canker diseases.

In an embodiment, the release rate of the first and/or second component can be controlled so that characteristics of one or both can be effective for time frames of days to weeks or to months. In other words, the first component and/or second component can be released from the multifunctional silica based nanoparticle or gel starting from the day of application and continuing release to about a week, about a month, about two months, about three months, about four months, about five months, about six months, about seven month, or about eight months.

The multifunctional silica based nanoparticle includes a core and shell. The core includes silica loaded with a first type of first component (e.g., Cu ions). The silica shell that can support a second type of first component (e.g., copper oxide), while also including the first component (e.g., Cu ions). Although not intending to be bound by theory, in an embodiment the second component can interact with the first component (e.g., Cu ions) via a charge-transfer type of interaction, where interaction between the first component and the second component can occur in the nanoparticle and/or in the amorphous silica material.

In an embodiment, the first component can include a copper component, a zinc component, a titanium component, a cerium component, a magnesium component, a zirconium component, polyethyleneimine (PEI), a carbon component (e.g., mixed carbon or soot), fullerene, carbon nanotubes, and a combination thereof. Specifically, the first component can include a copper ion, metallic copper (Cu), copper salt, copper complex, a zinc ion, metallic zinc (Zn), zinc oxide, zinc salt, a silver ion, metallic silver (Ag), silver salt, silver complex, a titanium ion, titanium dioxide ($TiO_2$), a cerium ion, cerium oxides, a magnesium ion, magnesium oxide, a zirconium ion, zirconium oxide, and a combination thereof.

In an embodiment, the copper component can include a copper ion, metallic copper, copper oxide, copper oxychloride, copper sulfate, copper hydroxide, and a combination thereof. The copper component can include copper ions that are electrostatically bound to the silica nanoparticle core or amorphous silica matrix, copper covalently bound to the hydrated surface of the nanoparticle or amorphous silica matrix, and/or copper oxides and/or hydroxides bound to the surface of the nanoparticle or amorphous silica matrix. In an embodiment, the multifunctional silica based nanoparticle and/or gel includes the copper component in two or in all three of these states.

In an embodiment, the copper component can be in a soluble (amorphous) and an insoluble (crystalline) form. By controlling the soluble and insoluble ratio, the release rate of the copper component can be controlled as a function of time. As a result, the release rate of the copper component can be controlled so that antibacterial and/or antifungal characteristics can be effective for time frames of days to weeks or to months. In other words, the copper component can be released from the multifunctional silica based nanoparticle or gel staring from the day of application and continuing release to about a week, about a month, about two months, about three months, about four months, about five months, about six months, about seven month, or about eight months. The ratio of the soluble to insoluble copper component can be adjusted to control the release rate. In an embodiment, the ratio of the soluble copper to the insoluble copper (e.g., Chelated $Cu)_X$ (Crystalline $Cu)_{1-X}$) can be out 0:1 to 1:0, and can be modified in increments of about 0.01 to produce the ratio that releases the Cu for the desired period of time. Parameters that can be used to adjust the ratio include: solvent polarity and protic nature (i.e., hydrogen bonding capability), Cu precursor (e.g., Cu sulfate) concentration, temperature, concentration of silane precursor (such as tetraethylorthosilicate, TEOS), and the like.

In an embodiment, the second component can include a sulfur compound. The sulfur compound does not react or reacts very little (e.g., at such a low percentage or at such a slow rate that the first and second components can still function in a manner and for a time frame described herein) with the first component. The sulfur compound can include alkyl sulfides, alkyl disulfides, alkyl trisulfides, alkyl tetrasulfides, analogues of each, and a combination thereof, where alkyl can include alkyl, dialkyl, and trialkyl. In particular, the sulfur compound can include compounds dimethyl disulfide (DMDS), dimethyl sulfide, diethyl disulfide, diethyl trisulfide, diethyl tetrasulfide, and a combination thereof. The release rate of the second component can be controlled to release starting from the day of application to about a week, about a month, about two months, about three months, about four months, about five months, about six months, about seven month, or about eight months.

In an embodiment, the sulfur compound is DMDS. It should be noted that the sulfur compound can be used as a ACP repellant and is attractive strategy to control the HLB. It should be noted that DMDS is toxic to insects because it disrupts cytochrome oxidase system of the mitochondria and is considered a strong repellent to ACP. DMDS can interact with the first component (e.g., Cu ion) in a charge-transfer type of interaction. Thus, by controlling the amount of first component that the DMDS can interact with, the amount of the first component can be used to control the amount of DMDS present in the multifunctional silica based nanoparticle or gel. Although not intending to be bound by theory, sulfur (electronegative element, polarizable) in DMDS is weakly bound to copper ions (type of ion-dipole interaction). Once Cu is released from the product, DMDS will mostly release as there is no other strong interaction between DMDS and silica nanoparticle/nanogel matrix other than Van der Waals force.

In an embodiment, the amorphous silica gel has no ordered (e.g., defined) structure (opposite to crystalline structure) so an "amorphous gel" refers to gel material having amorphous structural composition. In an embodiment, the number of multifunctional silica based nanoparticle in a gram of multifunctional silica based nanoparticle gel can be difficult to accurately determine. However, the following provides some guidance.

Let's assume amorphous silica gel (completely dehydrated) including about 10 nm size (diameter) inter-connected particles as our test material. One could roughly estimate number of particles per gram of material in the following way:

Mass ($m$) of a single particle=density of the particle ($d$)×volume of the particle ($v$)

D=2.648 gm/cm$^3$ (approx)
V=(4/3) Pi $(\pi)(r)^3$
Where r is the radius of the particle.
$\pi$=3.14; r=(10/2 nm)=5 nm=5×10$^{-7}$ cm.
If we plug in these numbers, v=5.23×10$^{-19}$ cm$^3$
Then m=(5.23×10$^{-19}$ cm$^3$)(2.648 gm/cm$^3$)
Or, m=1.38×10$^{-18}$ gm The multifunctional nanoparticle/nanogel product contains two active components, DMDS and first component (e.g., Cu) and a second component (e.g., DMDS). Experimentally, we can load about 33 to 45 wt % of Cu in silica nanoparticle material (measured by ICP-AAS analysis; ICP stands for Inductively Coupled Plasma-Atomic Absorption Spectroscopy). For example, Cu loading is about 33% in Cu loaded silica nanogel material synthesized in acidic ethanol-water mixture containing ethanol (95%) up to 45.5% of total volume. Cu loading is about 45% in Cu loaded silica nanoparticle material synthesized only in acidic water. Roughly one Cu can hold at least one DMDS molecule. These estimates can be applied to the first component and the second component.

An embodiment of the multifunctional silica based nanoparticle and gel are described in PCT Patent Application US 2009/006496 entitled "Silica-based Antibacterial and Antifungal Nanoformulation", which is incorporated herein by reference. In addition, methods of making an embodiment of the multifunctional silica based nanoparticle and gel are described in the aforementioned PCT Patent Application.

In general, the precursor material to make the multifunctional silica based nanoparticles and gel can be made by mixing a silane compound (e.g., alkyl silane, tetraethoxysilane, tetramethoxysilane, sodium silicate, or a silane precursor that can produce silicic acid or silicic acid like intermediates and a combination of these silane compounds) with a first component precursor compound in an acid medium (e.g., acidic water) that may contain an alcohol such as ethanol. After mixing for a period of time (e.g., about 30 minutes to a few hours), a mixture including silica nanoparticles loaded with the first component (also referred to as a "loaded silica nanoparticle") is formed. After the loaded silica nanoparticle are formed, the medium can be brought to a pH of about 7 and held for a time period (e.g., a few hours to a day) to form a precursor material that includes a loaded silica nanoparticle gel, where the nanoparticles are inter-connected. This process can be performed using a single reaction vessel or can use multiple reaction vessels.

Once the loaded silica nanoparticle is made, the multifunctional silica based nanoparticles and gel can be formed. The loaded silica nanoparticle can be disposed in a reaction vessel in an aqueous reaction medium (e.g., acidic water) or can be dried and mixed as a powder. The second component (e.g., DMDS) is also added to the reaction vessel that includes the aqueous reaction mixture or the dry precursor material. The ratio of the amount of precursor material and the second component (dry) can be about 1 to 1. This mixture is mixed for a period of time (e.g., from minutes to hours) to form the multifunctional silica based nanoparticles and gel. The multifunctional silica based nanoparticles and gel can be separated (e.g., centrifuge) from the aqueous solution and dried (e.g., air dried). The mixture does not require any additional purification, although further purification and processing can be performed. This process can be performed using a single reaction vessel or can use multiple reaction vessels and can be performed at ambient temperature and pressure.

In a particular embodiment, the second component is DMDS and can be added under mechanical stirring after Cu loaded silica nanoformulation is prepared. However, DMDS can be added anytime during the nanoformulation preparation process. In an embodiment, about 100 micrograms of DMDS is added to about 45 g equivalent of Cu.

In another embodiment of the present disclosure the multifunctional silica based nanoparticles gel can be formed using a second silane compound, where the addition of the second silane compound improves the uniformity of the plant surface coverage. During the step when the silane compound is added, the second silane compound can also be added. The second silane compound can include compounds such as alkyl silanes. The second silane compound can be about 0.01 to 30% or about 10 to 30% weight of the silane compound. The resulting silane mixture can include the first component and/or the second component, such as those described above. The nanoparticle is the same or similar to the nanoparticle described above and herein. It should be noted that an objective in this embodiment is to tailor nanoparticle/nanogel surface hydrophilicity or hydrophobicity to further improve adherence property of nanoformulations. For example citrus leaves are waxy (hydrophobic). To improve adherence of nanoformulation to waxy surface via hydrophobic-hydrophobic interaction, silica nanoparticle/nanogel material can be further modified with a hydrophobic silane reagent such methyl- or propyl- or butyl silane.

As mentioned above, embodiments of the present disclosure are effective for the treatment of diseases affecting plants such as citrus plants and trees. In addition, embodiments of the present disclosure can be effective as a protective barrier against phloem-feeding ACPs as it uniformly covers the plant surface (e.g., leaf surface). In particular, embodiments of the present disclosure can be used to combat citrus canker and greening diseases (HLB). The design of the multifunctional silica based nanoparticle or gel facilitate uniform plant surface coverage or substantially uniform plant surface coverage. In an embodiment, the multifunctional silica based nanoparticle or gel that is applied to plants can have a superior adherence property in various types of exposure to atmospheric conditions such as rain, wind, snow, and sunlight, such that it is not substantially removed over the time frame of the release of the first and/or second components. In an embodiment, the multifunctional silica based nanoparticle or gel has a reduced phytotoxic effect on plants and reduced environmental stress due to minimal Cu content.

Embodiments of the present disclosure can applied on the time frames consistent with the release of the first and second components, and these time frames can include from the first day of application to about a week, about a month, about two months, about three months, about four months, about five months, about six months, about seven month, or about eight months.

A specific embodiment of the multifunctional silica based nanoparticle or gel can include a multifunctional dimethyl disulfide (DMDS) and copper co-loaded silica based nanoparticle or nanogel (DMDS-CuSiNP/NG), which can be used to combat citrus canker and greening diseases is disclosed. When the composition is applied to citrus plants, it is effective for simultaneously controlling citrus canker and citrus greening diseases in a single application during one citrus growing season.

EXAMPLES

Now having described the embodiments of the present disclosure, in general, the examples describe some additional embodiments of the present disclosure. While embodiments of the present disclosure are described in connection with examples and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

CuSiNG Material and Properties

Laboratory-based experimental data confirmed the following: (i) much improved antibacterial properties of CuSiNG material in comparison to controls, Kocide® 3000 (a DuPont product; Cu hydroxide material) and Cu sulfate, (ii) exceptionally strong adherence property to the citrus leaf surface in comparison to controls and (iii) improved surface coverage, uniform throughout, upon spray application. Based on materials characterization data (High Resolution Transmission electron Microscopy and Selected Area Electron Diffraction patterns), it is confirmed that Cu is present in silica nanogel (SiNG) matrix in two different forms and in two different oxidation states, crystalline Cu oxide (Cu+1 state) and amorphous Cu complex (Cu+2 state). The CuSiNG is thus a unique, nanotechnology-enabled engineered nanomaterial. The disc diffusion assay confirmed that the CuSiNG material has the ability to diffuse out from the application location. This diffusion property will have strong impact in protecting rapidly expanding young fruit and leaf surfaces.

Example 2

DMDS Loaded CuSiNG in Solution

In the present disclosure, DMDS and Cu co-loaded silica nanogel (DMDS-CuSiNG) based materials and related formulations are prepared. Multidisciplinary research is used to develop and study DMDS loaded materials, conduct a number of laboratory based bioassays to test the efficacy and perform field study to evaluate the efficacy in controlling HLB and citrus canker diseases.

The loading of DMDS in CuSiNG has been studied in solution state (as synthesized CuSiNG liquid formulation) and characterized by the Gas Chromatography-Mass Spectrometry (GC-MS). In solution state, loading of DMDS into CuSiNG material was carried out by directly adding DMDS into the aqueous reaction mixture that contains CuSiNG material. Stirring was continued to ensure uniform mixing of DMDS with the CuSiNG material. The reaction medium composition greatly facilitated direct loading of DMDS into CuSiNG material. After 24 hrs, DMDS-CuSiNG material was centrifuged and air-dried for more than seven days. We were able to smell strong sulphur odor.

Figure 1B:
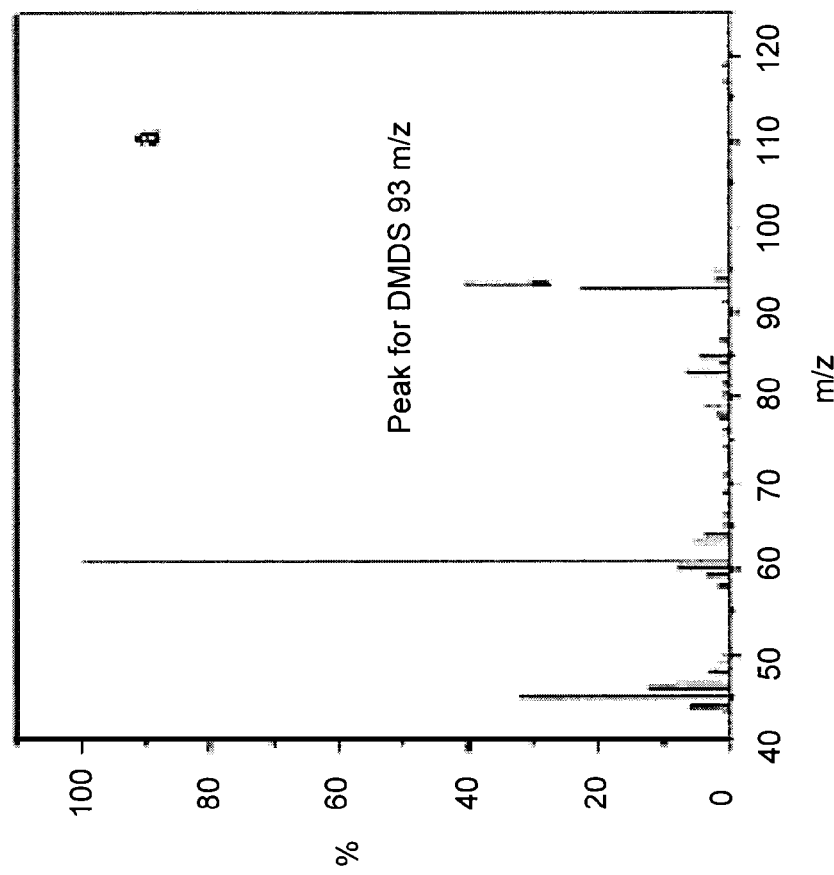
FIG. 1b is a plot of gas chromatography-mass spectroscopy (GC-MS) data of a chloroform extract of DMDS-CuSiNG.
Figure 2:
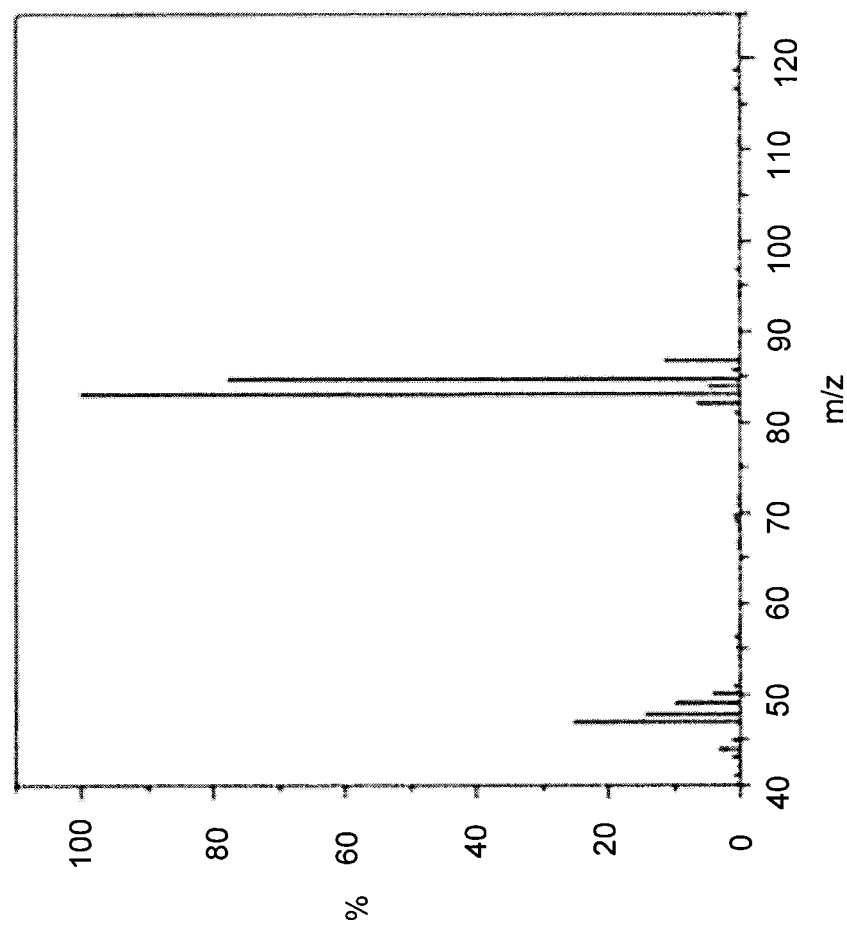
FIG. 2 is a plot of gas chromatography-mass spectroscopy (GC-MS) data of a chloroform extract of DMDS-SiNG, no copper ions.

FIG. 1a is GC-MS spectra of DMDS used as a control under conditions wherein the silica nanogel (SiNG) does not contain copper. FIG. 1b is a GC-MS spectra of DMDS-CuSiNG material. A DMDS odor from the DMDS-CuSiNG powder is discernable even after seven days. For GC-MS sample preparation, spectroscopy grade chloroform was added to the powder and DMDS. GC-MS data of DMDS (control) and chloroform extract of DMDS-CuSiNG are shown in FIG. 1a and FIG. 1b, respectively. Characteristic molecular peak for DMDS at 93 (m/z) along with other peaks for its fragmented structure is shown in FIG. 2 where the GC-MS spectra of DMDS-SiNG material products were found in both cases, confirming the presence of DMDS in DMDS-CuSiNG sample.

Similar experiment was also carried out with SiNG (instead of CuSiNG). After 3 days, we were not able to detect characteristic DMDS odor from DMDS-SiNG material and GC-MS study showed no noticeable DMDS characteristic peaks as shown in FIG. 2. These results suggest that $Cu^{2+}$ ions play a critical role with DMDS loading and retention.

Example 3

Loading of DMDS into CuSiNG in Dry State

Loading of DMDS in dry state using lyophilized CuSiNG powder was carried out by adding DMDS (100 μl neat) directly to CuSiNG (150 mg of vacuum dried powder) sample in a 20 mL glass vial. For a quick comparison purposes, we took 100 μl neat DMDS in another 20 mL glass vial (control). Both vials were kept side-by-side inside a laboratory fume hood to allow DMDS to evaporate at the same rate. After 3 days, we were able to smell strong DMDS odor from the DMDS-treated CuSiNG sample only.

Figure 3B:
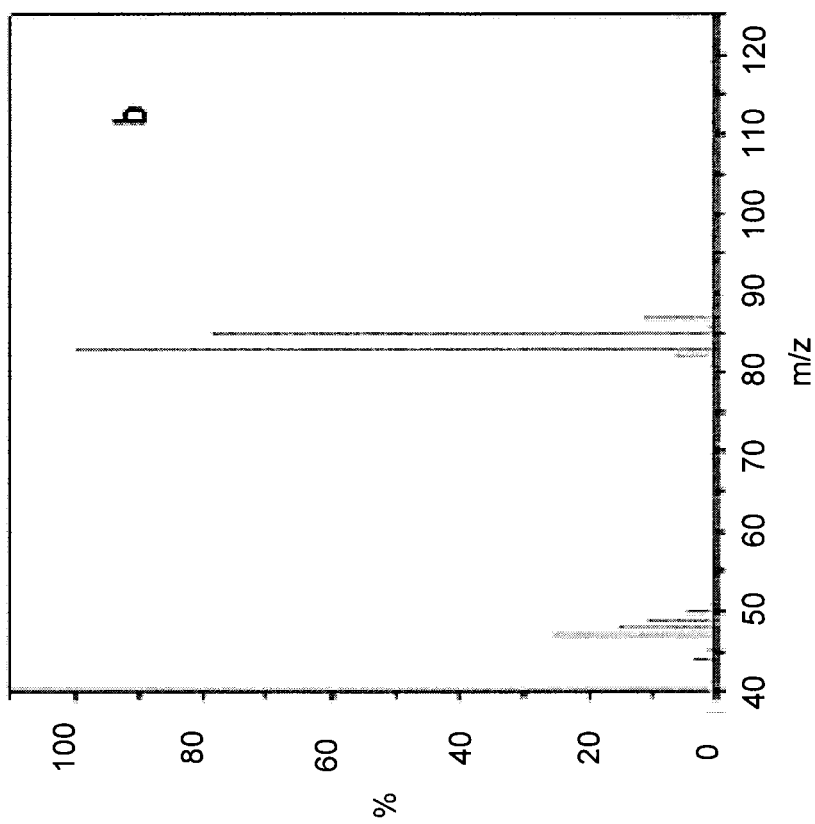
FIG. 3b is a plot of gas chromatography-mass spectroscopy (GC-MS) data of a chloroform extract of DMDS added to dry SiNG as a control showing no DMDS peaks.
Figure 3A:
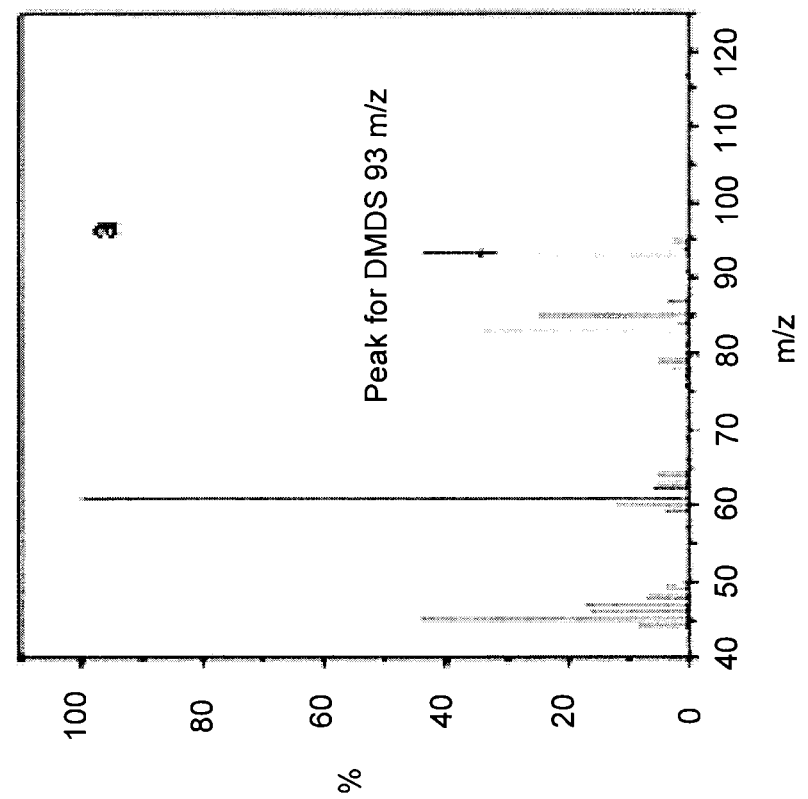
FIG. 3a is a plot of gas chromatography-mass spectroscopy (GC-MS) data of a chloroform extract of DMDS added to dry CuSiNG lyophilized powder with characteristic DMDS peaks shown.

Subsequently, chloroform is added to both vials and results are shown in FIGS. 3a and 3b. GC-MS spectra of DMDS added to dry CuSiNG lyophilized powder is shown in FIG. 3a. In FIG. 3b a control extract of DMDS is taken and performed GC-MS. As expected, characteristic DMDS peaks were obtained from DMDS-CuSiNG sample (FIG. 3a) and no such peaks from the control (FIG. 3b). The above preliminary experiments thus confirmed that CuSiNG material is able to load, retain and slowly release DMDS. A synthesis method for preparation of a silica matrix with embedded metallic particles is reported in U.S. Pat. No. 6,548,264 to Tan et al., U.S. Pat. No. 6,924,116 to Tan et al., and U.S. Pat. No. 7,332,351 to Tan et al., which are incorporated herein by reference. The synthesis of CuSiNG is disclosed in International Patent Application No. PCT/US2009/006496 filed Dec. 10, 2009 and is incorporated herein by reference.

Example 4

Characterization of DMDS-CuSiNG Material

The following material characterization techniques were used to characterize the DMDS-CuSiNG material of the present disclosure. First a GC-MS study will qualitatively confirm loading of DMDS in CuSiNG and SiNG materials. Second Quartz Crystal Microbalance (QCM) based sensing study will confirm loading and release of DMDS in real-time. Considering practical application of DMDS-CuSiNG material in the field, it is desirable to perform quantitative study to monitor DMDS loading/release processes in real-time. Therefore QCM based sensing technology will be adapted for quantitative measurements of DMDS loading/release and determine kinetics. The sensitivity of QCM technique is reported at the parts per billion level by J. W. Gardner et al, "A brief-history of electronic noses." *Sensors and Actuators B-Chemical* 1994, 18, (1-3), 211-220. The characterization of DMDS-CuSiNG clarifies the nature of interaction of DMDS with the CuSiNG material. Our goal is to investigate the physico-chemical environment around DMDS and the role of Cu in DMDS adsorption.

Briefly, the experimental setup includes using a sample of CuSiNG material that is spray-coated onto QCM sensor followed by exposure to DMDS in a closed chamber. It is expected that with time the resonating frequency of the QCM will continue to decrease as more and more DMDS is loaded into the CuSiNG material. Once equilibrium is reached, no further frequency drop will take place. The sensor is removed from the chamber and monitoring of the DMDS release process with time is observed. We expect to observe increase in frequency as more and more DMDS is released. Similar experiments will be performed for the SiNG material, as a control.

Example 5

Role of Cu II Ions in DMDS Loading

DMDS loading into SiNG matrix is driven by hydrogen bonding between the silica surface/pores containing silanol (—Si—OH) group (proton donor) and DMDS sulfur atom (proton acceptor), according to R. W. Glass, et al, in "Surface studies of adsorption of sulfur-containing gases at 423 degree K on porous adsorbents. 1. Adsorption of hydrogen sulfide, methanethiol, ethanethiol, and dimethyl sulfide on silica gels." *Journal of Physical Chemistry* 1973, 77, (21), 2571-2576.

Unlike SiNG, the physico-chemical environment of DMDS in CuSiNG is expected to be somewhat different due to presence of Cu (II) ions. Preliminary results suggest that characteristic odor DMDS does not change over time which indicates that DMDS is non-reactive to Cu(II) ions. However, the DMDS electron-rich sulfur atom has the ability to weakly interact with electron-deficient Cu(II) ion. This could further facilitate adsorption of DMDS into CuSiNG. Thorough FT-IR studies are performed to understand the nature of intermolecular interactions that exist between DMDS and SiNG. In addition, thermogravimetric analysis (TGA), calorimetry and QCM sensing studies to obtain DMDS loading/release characteristics (isotherms) against CuSiNG and SiNG materials will be used to determine the role of Cu II ions in DMDS loading. A comparative isotherm data analysis along with FT-IR analysis will reveal the effect of Cu in DMDS loading/release process.

Example 6

DMDS Loading into CuSiNG Through Nanoscale Manipulation

The manipulation of the molecular environment around DMDS at the nanoscale level was conducted to improve DMDS loading efficiency into CuSiNG and SiNG materials.

First hybrid silica nanogel (HSiNG) and Cu loaded HSiNG (CuHSiNG) materials were synthesized. A combination of two inexpensive silica precursors were used during the HSiNG synthesis consisting of a silane based ester and an alkyl based (e.g. methyl or propyl) silane. The rationale of introducing small alkyl chain polymers into the silica matrix is that it will improve interaction with DMDS via intermolecular hydrophobic-hydrophobic interaction.

A series of experiments were performed by varying the ratio of these two silica precursors to optimize loading of both Cu and DMDS into HSiNG material. Both the DMDS-HSiNG and DMDS-HCuSiNG materials are systematically characterized. DMDS loading efficiency to HSiNG and HCuSiNG materials will be evaluated and results will be compared with DMDS-CuSiNG material. For bioassays and field trials, only one DMDS-CuSiNG material that has maximum loading of Cu and DMDS will be selected, the two active components responsible for preventing canker and HLB diseases, respectively.

Characterization: Cu loading efficiency will be quantitatively determined by the atomic absorption spectroscopy (AAS) whereas DMDS loading/release kinetics will be determined by the QCM study. In addition, several material characterization techniques such as TEM/HRTEM (size and morphology), SAED (crystallinity), XPS (identification of Cu oxidation states), XRD (bulk crystallinity), SEM-EDAX (elemental analysis for estimating Cu to Si ratio), BET (surface area/porosity measurements) and FTIR (studying interaction of DMDS as well as Cu with silica matrix) will be used for systematic characterization of HSiNG and CuHSiNG materials. Further improvement of DMDS loading into HSiNG and HCuSiNG is expected due to additional hydrophobic-hydrophobic intermolecular interactions between the methyl groups of DMDS and alkyl groups of silane precursor.

Example 7

Comparing Efficacy of DMDS-CuSiNG and DMDS-HCuSiNG

Laboratory bioassays for efficacy evaluation of DMDS loaded materials include, disc diffusion assays against *X. alfalfae* and Olfactometer bioassays against ACPs and the disc diffusion assay. To test anti-bacterial activity of the DMDS-CuSiNG and DMDS-HCuSiNG materials, a known 'disc diffusion assay' method is used.

Briefly, appropriate dilution of overnight grown *X. alfalfae* culture (200 μl of about 106 cfu/ml based on dilution of the 0.5 Mc Farland standard) will be spread on nutrient agar plates (90 mm) to achieve a confluent lawn of growth. Comparative analysis of growth inhibition by different concentrations of the test materials (DMDS-CuSiNG and DMDS-HcuSiNG) using DMDS-SiNG and DMDS-HSING as negative controls, and Cu sulfate and Kocide® 3000 as positive controls will be performed to find out the difference in minimum inhibitory concentration ranges under the test conditions. The same volume containing different concentrations of each formulation will be applied per disc to avoid any variation of unequal diffusion perimeter on the agar plate. The level of anti-bacterial ability will be determined by measuring the zone of inhibition after 24 hrs of incubation at 30° C. The minimum inhibitory concentration (MIC) of all the above mentioned compounds, including DMDS-CuSiNG and DMDS-HCuSiNG, will also be determined by spreading appropriate dilution of *X. alfalfae* culture on nutrient agar plates containing $\log^2$ (two fold) serial dilutions of the test compound(s) to correlate the results of the zone of inhibition in the disc diffusion test and to refine the concentration of DMDS-CuSiNG and DMDS-HCuSiNG necessary for effective killing of the pathogens.

All the test plates will be incubated for longer periods beyond 24 hours to detect any delayed growth of the test organism by the formation of isolated colonies in the zone of inhibition or on the dilution series agar plates at the MIC level. This will tentatively indicate the difference in stability between the DMDS-CuSiNG (or DMDS-HCuSiNG) and Kocide® 3000 or Cu sulfate under the test conditions, which will be an indirect evaluation of the difference in Cu release kinetics of the DMDS-CuSiNG (or DMDS-HCuSiNG) and the Kocide® 3000. We will also generate dose-response plots wherever appropriate. Briefly, dosage of the Cu compound will be varied and the relative response or percentages of disease control to those dosages will be determined.

Statistical analysis: We will test the significance of anti-bacterial activity by different statistical analyses such as ANNOVA discussed in *Design and Analysis of Experiments* by Hinkelmann, K.; Kempthorne, O., Wiley: 2008; Vol. I and II (Second ed.). Diameter of inhibition zone with all the respective anti-bacterial materials at different concentrations and incubation times will be measured to use in the statistical analysis, assessing the suitability of CuSiNG and H—CuSiNG as a better anti-bacterial material with respect to the controls.

The benefits of applying nanotechnology in citrus research are enormously high. Silica nanogel matrix provides a unique environment for co-hosting Cu and DMDS, making DMDS-CuSiNG nanomaterial multifunctional for combating both citrus canker and greening diseases. Recent studies suggest that silica nanogel is able to slowly spread out from the point of application in moist environment. The impact would be tremendously high as this CuSiNG will form a uniform film-like coating on the surface over time. We identify two major advantages of silica nanogel film; (i) ability to protect rapidly growing young fruit and leaf surfaces and (ii) ability to serve as protective barrier for phloem-feeding ACPs.

The DMDS-CuSiNG technology will offer the following benefits: (a) a two-in-one formulation for combating both citrus canker and greening, (b) superior Cu bioavailability and longevity, (c) sustained release of DMDS for protecting invasion of ACP (primary defense mechanism), (d) robust coating of DMDS-CuSiNG onto leaf surface (secondary defense mechanism against ACP), (e) simple one-pot bulk synthesis technique, (f) inexpensive ingredients (raw material cost ~$3.00 per acre) and (g) multiple applications are not required.

Due to nanoscale engineering, the CuSiNG of the present disclosure has the following advantages over the existing Cu based compounds: uniform coverage of plant surface because of ultra-small particle size, better adherence property due to gel-like nanostructure, sustained (long-term) Cu release profile, better control on Cu release rate (adjustable "soluble" to "insoluble" Cu ratio), more antibacterial/antifungal activity with less amount of Cu content, reduced phytotoxic effect because of adjustable "soluble" to "insoluble" Cu ratio and environment-safe due to less Cu content, no harmful by-product formation, water-based synthesis, utilization of excess CuSiNG as plant nutrient and minimal possibility of having elevated local Cu concentration that could cause environmental toxicity.

The synthesis protocol has the following advantages: (i) simplicity, (ii) water-based, (ii) scalable to field applications, (iii) single-pot synthesis method, requiring no purification steps and (v) concentrated CuSiNG material could be easily diluted for field application. A non-technical person can do this task by adding an appropriate amount of water, thus reducing shipping costs. The method also uses inexpensive raw chemicals and is easily produced in a cost-effective manner.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

I claim:

1. A composition, comprising
a multifunctional silica based nanoparticle including a first component and a second component, wherein the multifunctional silica based nanoparticle includes a silica core and a silica shell, wherein the core includes a first type of the first component, wherein the shell includes a second type of the first component, wherein the first component functions as an antibacterial, an antifungal, or a combination thereof, wherein the second component functions as a repellant for insects.

2. The composition of claim 1, wherein the first component is selected from a copper component, a zinc component, a titanium component, a cerium component, a magnesium component, a zirconium component, a polyethyleneimine (PEI), a fullerene, a carbon nanotube, and a combination thereof; and the second component is a sulfur compound.

3. The composition of claim 2, wherein the sulfur component is selected from: an alkyl sulfide, an alkyl disulfide, an alkyl trisulfide, an alkyl tetrasulfide, and a combination thereof.

4. The composition of claim 2, wherein the sulfur component is selected from: dimethyl disulfide (DMDS), dimethyl sulfide, diethyl disulfide, diethyl trisulfide, diethyl tetrasulfide, and a combination thereof.

5. The composition of claim 4, wherein the first component is a copper component.

6. The composition of claim 5, wherein the copper component is selected from copper ion, metallic copper, copper oxide, copper oxychloride, copper sulfate, copper hydroxide, and a combination thereof.

7. The composition of claim 6, wherein the sulfur component is selected from: an alkyl sulfide, an alkyl disulfide, an alkyl trisulfide, an alkyl tetrasulfide, and a combination thereof.

8. The composition of claim 6, wherein the sulfur component is selected from: dimethyl disulfide (DMDS), dimethyl sulfide, diethyl disulfide, diethyl trisulfide, diethyl tetrasulfide, and a combination thereof.

9. The composition of claim 6, wherein the sulfur component is dimethyl disulfide (DMDS).

10. The composition of claim 9, wherein the DMDS is attached to the multifunctional silica based nanoparticle via copper ions.

11. A gel comprising:
a plurality of multifunctional silica based nanoparticles disposed in an amorphous silica material, a multifunctional silica based nanoparticle including a first component and a second component, wherein the multifunctional silica based nanoparticle includes a core and a shell, wherein the core includes a first type of the first component, wherein the shell includes a second type of the first component, wherein the first component functions as an antibacterial, an antifungal, or a combination thereof, wherein the second component functions as a repellant for insects, wherein the amorphous silica material also includes one or both of the first component and the second component.

12. The gel of claim 11, further comprising a silane compound.

13. The gel of claim 12, wherein the second silane compound is selected from the group consisting of: 3-(trihydroxysilyl)propyl methylphosphate, alkyl silane, tetraethoxysilane, tetramethoxysilane, sodium silicate, a silane precursor that can produce silicic acid or silicic acid like intermediates, and a combination thereof.

* * * * *